United States Patent [19]

Fukuoka et al.

[11] Patent Number: 4,552,974

[45] Date of Patent: Nov. 12, 1985

[54] PROCESS FOR PRODUCING DIPHENYLMETHANE DICARBAMATES

[75] Inventors: Shinsuke Fukuoka; Tomonari Watanabe, both of Okayama, Japan

[73] Assignee: Asahi Kasei Kogyo Kabushiki Kaisha, Osaka, Japan

[21] Appl. No.: 559,114

[22] Filed: Dec. 7, 1983

[30] Foreign Application Priority Data

Dec. 7, 1982 [JP] Japan .............................. 57-213424
Dec. 9, 1982 [JP] Japan .............................. 57-215911

[51] Int. Cl.$^4$ ................ C07C 125/073; C07C 125/075
[52] U.S. Cl. ...................................... 560/25; 560/21; 260/465 D
[58] Field of Search ................ 560/25, 21; 260/465 D

[56] References Cited

U.S. PATENT DOCUMENTS

| 4,146,727 | 3/1979 | Shawl et al. ........................... 560/25 |
| 4,243,815 | 1/1981 | Merger et al. ......................... 560/25 |
| 4,319,018 | 3/1982 | Miyata et al. ....................... 560/25 X |

FOREIGN PATENT DOCUMENTS

| 2044252 | 10/1980 | United Kingdom .................. 560/25 |
| 2054584 | 2/1981 | United Kingdom .................. 560/25 |

OTHER PUBLICATIONS

Merger, Chem. Abs., vol. 99, (1983), 140572g.

*Primary Examiner*—Bernard Helfin
*Attorney, Agent, or Firm*—Sughrue, Mion, Zinn Macpeak & Seas

[57] ABSTRACT

A process for producing a diphenylmethane dicarbamate by reacting an N-phenylcarbamate with a methylenating agent is disclosed. The process is carried out by condensing N-phenylcarbamate in two steps using a combination of two different types of acid catalysts. The catalysts exhibit a strong catalyzing effect and yet can be readily separated from the reaction mixture. The process produces dineuclear diphenylmethane dicarbamates in high selectivity. The acid catalysts can be easily recovered from the reaction mixtures and put to another use.

33 Claims, 2 Drawing Figures

PROCESS FOR PRODUCING DIPHENYLMETHANE DICARBAMATES

FIELD OF THE INVENTION

The present invention relates to a method of condensing N-phenylcarbamates, and more particularly, to an industrially advantageous method of producing dinuclear diphenylmethane dicarbamates in high selectivity by condensation of N-phenylcarbamates with a methylenating agent (i.e., an agent for introducing a methylene group) by way of a methylene group.

BACKGROUND OF THE INVENTION

Diphenylmethane dicarbamates are useful precursors for the preparation of diphenylmethane diisocyanates (MDI) without using phosgenes. Their derivative in 4,4'-form, namely, 4,4'-diphenylmethane diisocyanate, which is generally known as pure MDI, is an advantageous starting material for the production of polyurethane elastomers, spandex fibers and artificial leather coatings. There has been a rapid increase in demand for pure MDI. Therefore, there is a need to develop a commercial process for producing diphenylmethane dicarbamates from which the pure MDI can be manufactured.

Conventionally, these diphenylmethane dicarbamates are produced by reacting N-phenylcarbamates with a condensing agent such as formaldehyde, paraformaldehyde, methylal or trioxane in the presence of an acid such as mineral acid or organic sulfonic acid. If relatively severe conditions are used in this reaction, for example, if a strong acid is used in a large amount, the reaction temperature is high or the reaction period is extended, not only is the desired diphenylmethane dicarbamate produced but also polynuclear polymethylene polyphenylcarbamates having the following formula are produced in a significant amount:

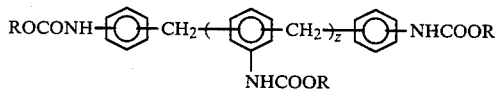

(wherein R is an alkyl group, aromatic group or an alicyclic group; z is an integer of 1 or more). Furthermore, if a strong liquid acid is used much difficulty and hence a lot of cost is entailed in separating the acid from the reaction mixture and recovering the same in a reusable form.

In order to eliminate this defect with the recovery of acids, a method was proposed for using an aqueous acid solution having a concentration of 10% or higher (British Pat. No. 2,044,252, Japanese Patent (OPI) Nos. 81850/80 and 81851/80 and Chemical Abstracts 93 169057e). This method is effective for acid recovery because as shown in their working examples, if aqueous acid solutions having a concentration of not more than 50% are used, the acid can fairly easily be separated from the organic phase in the form of layers. However, the presence of a great amount of water renders it difficult to complete the reaction without leaving a significant amount of compounds having a methylene-amino bond(—CH$_2$—N<) wherein the methylene group is bonded to the nitrogen atom in the carbamate group. In order to complete the reaction without these compounds, less water must be used to increase the acid concentration to, for example, 80% or higher. However, this causes the hydrolysis of the starting compound or the reaction product, or leaves them to dissolve in the concentrated aqueous acid solution in a large quantity, and as a result, the separation of the product from the acid solution becomes difficult.

In any event, it is not industrially advantageous to carry out a one-step condensation of N-phenylcarbamates with an aqueous solution of acid and to use the resulting product in the preparation of isocyanates. More specifically, dinuclear, trinuclear or other polynuclear compounds having the methylene-amino bond cannot be easily separated from the condensation product containing diphenylmethane dicarbamates and polymethylene polyphenylcarbamates. If the condensation product containing these compounds with the methylene-amino bond is decomposed thermally, these compounds do not provide the desired isocyanates. Furthermore, they enter into various side reactions with the isocyanates derived from the carbamates such as diphenylmethane dicarbamates, and in consequence, the yields of the desired isocyanates are reduced. In addition, the resulting byproducts cannot be easily separated from the desired isocyanates, particularly, the polynuclear polymethylene polyphenyl isocyanates, and they are in all cases present in the final product generally referred to as a polymeric isocyanate, and properties of the product are impaired.

It is therefore necessary to perform the condensation of N-phenylcarbamates in such a manner that a minimum amount of the compounds with the methylene-amino bond is left in the condensation product. One method that has been proposed for attaining this object is described in U.S. Pat. No. 4,146,727, wherein these compounds within the methylene-amino bond are subjected to a rearrangement reaction, under substantially anhydrous conditions, with a protonic acid catalyst having a strength of at least the magnitude of a 75% sulfuric acid, or a Lewis acid at a temperature of 50° to 170° C. so as to rearrange the methylene group, which was bonded to the nitrogen atom, to bond to the benzene ring. However, this method must use a large amount of concentrated sulfuric acid or paratoluenesulfonic acid and again requires complicated procedures and great cost for separating and recovering these acids from the reaction mixture.

Japanese Patent (OPI) No. 7749/81 and Chemical Abstracts, 94 209480s propose a method for producing polymethylene polyphenylcarbamate by heating only bis(N-carboalkoxyanilino)methane, which is a compound having the methylene-amino bond, in the presence of an acid catalyst. However, this method is not ideal for selective production of the diphenylmethane dicarbamate because it causes not only the desired rearrangement reaction but also the undesired condenstion reaction, and trinuclear and other polynuclear polymethylene polyphenylcarbamates are formed as byproducts in addition to the desired diphenylmethane dicarbamate. Furthermore, the reaction is slow and the rearrangement reaction is not completed without leaving the residual bis(N-carboalkoxyanilino)methane in the reaction product.

U.S. Pat. No. 4,319,018, British Pat. No. 2,054,584, Japanese Patent (OPI) No. 12357/81 and Chemical Abstracts, 94 124715t propose a method for producing diphenylmethane dicarbamates and polymethylene polyphenyl carbamates by reacting N-phenylcarbamates with formaldehyde or its precursor in the presence of both an acid catalyst and the compounds having the methylene-amino bond. However, this method is unable to reduce the content of the compounds with the methylene-amino bond, and the compounds are unavoidably left in the condensation product in an amount as much as ten-odd percent by weight.

SUMMARY OF THE INVENTION

The present inventors have therefore made extensive studies to develop an industrially advantageous condensation process capable of producing dinuclear diphenylmethane dicarbamates in high selectivity without the defects of the conventional techniques. As a result, the inventors have found that this object can be attained by condensing an N-phenylcarbamate in two steps using a combination of two different types of acid catalysts that can exhibit their catalyzing effects to the utmost extent and which yet can be readily separated from the reaction mixture.

Therefore, the present invention relates to a process for producing a diphenylmethane dicarbamate by reacting an N-phenylcarbamate with a methylenating agent, the process comprising:

(A) the first reaction step wherein a methylenating agent is reacted in liquid phase with at least 2 mols of an N-phenylcarbamate per mol equivalent of the methylene group of the methylenating agent in the presence of an aqueous solution of an inorganic acid either alone or in combination with an organic solvent;

(B) the first separation step wherein the reaction mixture produced in the first reaction step is separated into the aqueous solution of an inorganic acid and an organic-phase reaction mixture substantially free from the inorganic acid;

(C) the second reaction step wherein said organic-phase reaction mixture containing the intermediate compounds having the methylene-amino bond (—CH$_2$—N<) is subjected to heat treatment in the presence of an N-phenylcarbamate and a carboxylic acid which has a pKa of not more than 4 in an aqueous solution at 25° C. or a solid acid or a mixture of the carboxylic acid and solid acid, in order to convert the intermediate compounds to the desired diphenylmethane dicarbamates by the intermolecular transfer reaction of the intermediate compounds with the N-phenylcarbamate; and (D) the second separation step wherein the reaction mixture produced in the second reaction step is separated from the carboxylic acid and/or the solid acid.

The present invention also relates to a process for producing a diphenylmethane dicarbamate by reacting an N-phenylcarbamate with a methylenating agent, the process comprising;

(A) the first reaction step wherein a methylenating agent is reacted in liquid phase at a temperature between 40° and 150° C. with 2 to 10 mols of an N-phenylcarbamate per mol equivalent of the methylene group of the methylenating agent in the presence of an aqueous solution of an inorganic acid either alone or in combination with an organic solvent;

(B) the first separation step wherein the reaction mixture produced in the first reaction step is separated into the aqueous solution of an inorganic acid and an organic-phase reaction mixture substantially free from the inorganic acid and methylenating agent, and the separated aqueous solution of the inorganic acid is returned to the first reaction step after optionally adjusting the concentration of the inorganic acid to a predetermined value;

(C) the second reaction step wherein the organic-phase reaction mixture containing the intermediate compounds having the methylene-amino bond (—CH$_2$—N<) is subjected to heat treatment at a temperature between 40° and 200° C. in the presence of an N-phenylcarbamate and a carboxylic acid which has a pKa of not more than 4 in an aqueous solution at 25° C., in order to convert the intermediate compounds to the desired diphenylmethane dicarbamates by the intermolecular transfer reaction of the intermediate compounds with the N-phenylcarbamate; and (D) the second separation step wherein the carboxylic acid is separated from the reaction mixture produced in the second reaction step, and the separated carboxylic acid is returned to the second reaction step.

The present invention further relates to a process for producing a diphenylmethane dicarbamate by reacting an N-phenylcarbamate with a methylenating agent, the process comprising:

(A) the first reaction step wherein a methylenating agent is reacted in liquid phase at a temperature between 40° and 150° C. with 2 to 10 mols of an N-phenylcarbamate per mol equivalent of the methylene group of the methylenating agent in the presence of an aqueous solution of an inorganic acid either alone or in combination with an organic solvent;

(B) the first separation step wherein the reaction product produced in the first reaction step is separated into the aqueous solution of an inorganic acid and an organic-phase reaction mixture substantially free from the inorganic acid and methylenating agent, and the separated aqueous solution of the inorganic acid is returned to the first reaction step after optionally adjusting the concentration of the inorganic acid to a predetermined value; and (C) the second reaction/separation step wherein a reaction and separation is continuously carried out by first bringing the organic-phase reaction mixture containing the intermediate compounds having the methylene-amino bond (—CH$_2$—N<) into contact with a solid acid at a temperature between 40° and 200° C. that is retained within a reactor in the presence of an N-phenylcarbamate to convert the intermediate compounds to the desired diphenylmethane dicarbamates by intermolecular transfer reaction of the intermediate compounds with the N-phenylcarbamate, and subsequently withdrawing the resulting reaction mixture from the reactor.

One object of the present invention is to provide a commercially feasible process for producing from an N-phenylcarbamate and a methylenating agent a condensation product that mainly consists of a diphenylmethane dicarbamate, and optionally contains its higher homolog polymethylene polyphenylcarbamates, that is a suitable raw material for the production of the isocyanates by thermal decomposition which isocyanates mainly consist of diphenylmethane diisocyanate (MDI), and optionally contain its higher homologs polymethylene polyphenyl isocyanate (PMPPI).

Another object of the present invention is to provide a process for producing dinuclear diphenylmethane dicarbamates in high selectivity.

A further object of the present invention is to provide a process for producing dinuclear diphenylmethane dicarbamates wherein the acid catalysts used can be easily separated and recovered from the reaction mixture and can be readily put to another use.

It is essential for these purposes of the present invention that the first reaction step, the first separation step, the second reaction step to convert the intermediate compounds having the methylene-amino bond to the diphenylmethane dicarbamates by the intermolecular transfer reaction, and the second separation step defined above be combined.

DETAILED DESCRIPTION OF THE INVENTION

Figure 1:
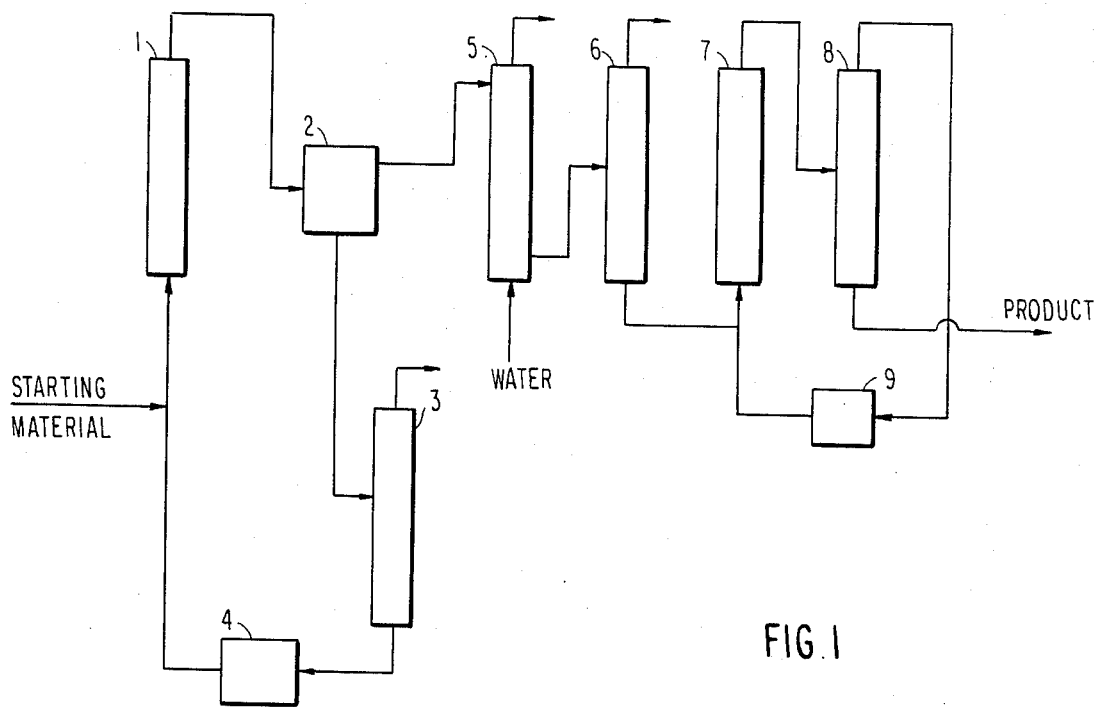
FIG. 1 is a schematic flow diagram showing one preferred embodiment of the present invention.

Within the drawings the reactor 1 for the first reaction step (A) is shown at the beginning of the reaction. The flow sheet then continues to at the separator 2 where the first separation step (B) is carried out. From the separator 2 the process may continue to the concentrator 3 for concentrating the aqueous solution of an inorganic acid and then continue to the tank 4 of the aqueous solution of inorganic acid. The process may then proceed to an extractor 5 for substantially removing the inorganic acid slightly contained in the organic-phase reaction solution, dehydrator 6, and a reactor 7 for the second reaction (C). After completing the second reaction (C) the process may proceed to a distillation column 8 for separating the carboxylic acid from the condensation product for use in the second reaction step and the carboxylic acid tank 9.

The N-phenylcarbamates used in the process of the present invention are the compounds represented by formula (I):

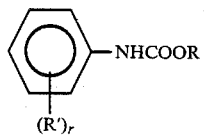

wherein R is an alkyl group having from 1 to 20 carbon atoms, preferably from 1 to 10 carbon atoms, aromatic group or an alicyclic group having 3 to 30 carbon atoms, preferably from 5 to 18 carbon atoms; R' is hydrogen or a substituent such as an alkyl group having from 1 to 20 carbon atoms, halogen atom, nitro group, cyano group, alkoxy group having from 1 to 20 carbon atoms or alicyclic group having from 3 to 20 carbon atoms, provided that these substituents are bonded at the ortho- or meta-position to the urethane group; r is an integer of 0 to 4; when r is 2 or more, R' may represent the same or different substituents; and at least one hydrogen in R may be substituted by any of the substituents listed above.

Preferred examples of R include alkyl groups such as methyl, ethyl, 2,2,2-trichloroethyl, 2,2,2-trifluoroethyl, propyl (n- or iso-), butyl (n- and various isomers), pentyl (n- and various isomers) and hexyl (n- and various isomers), alicyclic groups such as cyclopentyl and cyclohexyl and aromatic groups such as phenyl and naphthyl; and preferred examples of R' include hydrogen, the alkyl groups and alicyclic groups listed above, halogens such as fluorine, chlorine, bromine and iodine, nitro groups, cyano groups and alkoxy groups having the alkyl moieties listed above.

Preferred examples of the N-phenylcarbamates represented by formula (I) include methyl N-phenylcarbamate, ethyl N-phenylcarbamate, propyl N-phenylcarbamate (its isomers), butyl N-phenylcarbamate (its isomers), pentyl N-phenylcarbamate (its isomers), hexyl N-phenylcarbamate (its isomers), cyclohexyl N-phenylcarbamate, 2,2,2-trichloroethyl N-phenylcarbamate, 2,2,2-trifluoroethyl N-phenylcarbamate, methyl N-o- (or m-)tolylcarbamate, ethyl N-o-(or m-)tolycarbamate, 2,2,2-trifluoroethyl N-o- (or m-)tolycarbamate, propyl N-o- (or m-)tolylcarbamate (its isomers), butyl N-o- (or m-)tolylcarbamate (its isomers), methyl N-o- (or m-)chlorophenylcarbamate, ethyl N-o- (or m-)chlorophenylcarbamate, propyl N-o- (or m-)chlorophenylcarbamate (its isomers), butyl N-o- (or m-)chlorophenylcarbamate (its isomers), 2,2,2-trifluoroethyl N-o- (or m-)chlorophenylcarbamate, methyl N-2,6-dimethylphenylcarbamate, ethyl N-2,6-dimethylphenylcarbamate, propyl N-2,6-dimethylphenylcarbamate (its isomers), butyl N-2,6-dimethylphenylcarbamate (its isomers), 2,2,2-trifluoroethyl N-2,6-dimethylphenylcarbamate, methyl N-2,6-dibromophenylcarbamate, ethyl N-2,6-dibromophenylcarbamate, propyl N-2,6-dibromophenylcarbamate (its isomers), butyl N-2,6-dibromophenylcarbamate (its isomers), and 2,2,2-trifluoroethyl N-2,6-dibromophenylcarbamate.

Illustrative methylating agents that can be used in the present invention include formaldehyde, paraformaldehyde, trioxane, tetraoxane, dialkyloxymethane, diacyloxymethane, 1,3-dioxolane, 1,3-dioxane, 1,3-dithiane, 1,3-oxathiane, and hexamethylenetetramine. Preferred compounds are formaldehyde, paraformaldehyde, trioxane and dialkoxymethane having the lower alkyl groups of 1 to 6 carbon atoms such as dimethoxymethane, diethoxymethane, dipropoxymethane, dipentanoxymethane and dihexyloxymethane, as well as diacyloxymethanes having the lower acyloxy groups such as diacetoxymethane and dipropioxymethane. These methylenating agents may be used either alone or in combination. A particularly preferred methylenating agent is an aqueous solution of formaldehyde. One feature of the present invention is its ability to produce diphenylmethane dicarbamates in high selectivity using the least expensive methylenating agent such as an aqueous formaldehyde.

In the first reaction step of the present invention, the N-phenylcarbamate is reacted with the methylenating agent in the presence of a catalyst comprising an aqueous solution of an inorganic acid. Suitable inorganic acids include hydrochloric acid, sulfuric acid, phosphoric acid, polyphosphoric acid, heteropolyacid and boric acid. Sulfuric acid is particularly preferred. The concentration of the inorganic acid in its aqueous solution preferably ranges from 20 to 70 wt %, and the range of 30 to 60 wt% is particularly preferred. The most preferred is an aqueous solution containing 40 to 60 wt% of sulfuric acid. If the concentration of the inorganic acid exceeds 70 wt%, the N-phenylcarbamate and the condensation products are hydrolyzed to form the corresponding amino compounds. These amino compounds are not desirable since it causes various bad side reactions when the diphenylmethane dicarbamate produced is subsequently converted to an isocyanate by thermal decomposition. Furthermore, such a highly concentrated acid solution dissolves a significant amount of the starting materials and the reaction product therein, so that the separation of the organic phase from the mixture is performed only with complicated procedures. On the other hand, if the concentration of the inorganic acid is less than 20 wt%, the reaction is too slow to suit practical purposes.

In the first reaction step, at least 2 mols, preferably 2.2 to 10 mols, more preferably 2.5 to 6 mols, of the N-phenylcarbamate is used per mol equivalent of the methylene group of the methylenating agent. The aqueous solution of inorganic acid is used in such an amount that it preferably contains 0.01 to 20 mol equivalents, more preferably 0.05 to 15 mol equivalents, most preferably 0.1 to 10 mol equivalents, of the inorganic acid per mol equivalent of the N-phenylcarbamate.

The first reaction step of the present invention may be performed in a two-component dispersion made of organic and aqueous phases using water as the reaction medium. Alternatively, the reaction may be performed in a two-component dispersion made of an aqueous phase and an organic phase using an organic solvent. In either case, it is preferred that the most finely dispersed liquid droplets be formed throughout the reaction. Preferred organic solvents are those which have boiling points of not higher than 300° C. at atmospheric pressure and which have a mutual solubility with water of not more than 10% at room temperature. If organic solvents having a mutual solubility with water of not more than 10% are used, the organic phase containing the diphenylmethane dicarbamate and other condensates can be readily separated from the aqueous phase containing the inorganic acid by simple means such as phase separation after the first reaction. If, on the other hand, organic solvents having boiling points of not higher than 300° C. at atmospheric pressure are used, these solvents can be separated from the organic-phase reaction mixture by simple means such as distillation.

Preferred organic solvents include aromatic compounds having electron attracting substituents or halogen atoms. Suitable electron attracting substituents include nitro, cyano, alkoxycarbonyl, sulfonate, trifluoromethyl and trichloromethyl groups. These aromatic compounds are substantially inert to the electrophilic substitution of the methylene group under the conditions used for the first reaction step. Furthermore, these aromatic compounds have great ability to dissolve not only the N-phenylcarbamates (used as one of the starting materials) but also the diphenylmethane dicarbamates finally produced.

A particularly preferred electron attracting group is a nitro group. Preferred examples of the aromatic compounds having a nitro group or a halogen atom or both include nitrobenzene and lower alkyl substituted nitrobenzenes such as nitrotoluene (its isomers), nitroxylene (its isomers), nitromesitylene and nitroethylbenzene (its isomers); halogen substituted nitrobenzenes such as chloronitrobenzene (its isomers) and bromonitrobenzene (its isomers); halogenated benzenes such as chlorobenzene, dichlorobenzene (its isomers), trichlorobenzene (its isomers), bromobenzene, dibromobenzene (its isomers) and tribromobenzene (its isomers); halogenated naphthalenes such as chloronaphthalene (its isomers), dichloronaphthalene (its isomers) and bromonaphthalene (its isomers); and lower alkyl substituted halogenated benzenes such as chlorotoluene (its isomers), dichlorotoluene (its isomers), ethyl chlorobenzene (its isomers), chloroxylene (its isomers), bromotoluene (its isomers) and bromoxylene (its isomers).

In the first reaction step, the reaction is carried out at a temperature in the range of 40° to 150° C., preferably 60° to 130° C., more preferably 70° to 110° C. The pressure used herein is in the range of 0.5 to 20 kg/cm$^2$, preferably 0.8 to 10 kg/cm$^2$. Generally, the reaction is carried out under atmospheric pressure or under a low pressure. The reaction period varies with the type, the concentration and the amount of the aqueous solution of inorganic acid and the reaction temperature. The reaction period also depends on whether any organic solvent is used, or on the type of the reactor used. Since it is preferred that the smallest possible amount of the methylenating agent is left in the reaction mixture coming out of the first reaction step, the duration of the first reaction generally ranges from several minutes to several hours. The reaction may be performed either batchwise or continuously.

The reaction mixture obtained in the first reaction step is then fed to the first separation step (B) where it is separated into the aqueous solution of inorganic acid and an organic-phase reaction mixture substantially free from the inorganic acid, and the resulting aqueous solution of inorganic acid is returned to the first reaction step either immediately or after the adjustment of the aqueous solution of inorganic acid to the predetermined concentration if necessary.

While there is no particular limitation on the method of separating the aqueous solution of inorganic acid from the organic-phase reaction mixture, the simple phase-separation technique can be used for the purpose under the conditions specified for the present invention. The following phase-separation methods may be used: according to one method, the reaction mixture is cooled, without using an organic solvent, to a temperature close to or lower than room temperature, and in this case, the organic-phase reaction mixture forms a solid phase and can be readily separated from the aqueous solution of inorganic acid by simple means such as filtration. According to the other method, the reaction mixture is dissolved in the organic solvent described above or heated to a temperature over 50°–60° C., and in this case, two immiscible liquid phases (organic phase and aqueous phase) form and can readily be separated from each other.

The organic-phase reaction mixture thus separated from the aqueous solution of inorganic acid may sometimes contain a small amount of the inorganic acid, which is preferably removed by a suitable method such as washing with water. If the inorganic acid remains unremoved from the final condensation product, it causes the undesired side reactions or corrodes the reactor during the subsequent thermal decomposition of the condensation product for producing the isocyanates.

The concentration of the inorganic acid in its aqueous solution that has been separated from the organic-phase reaction mixture in the first separation step is generally lower than the initial value because water is produced in the first reaction step if a formaldehyde is used as the methylenating agent, and if an aqueous solution of formaldehyde is used, there also is a corresponding increase in the water content. Therefore, if one wants to perform the first reaction under constant conditions, the concentration of the inorganic acid must be increased to a predetermined level for re-use. For the purposes of the present invention, the preferred concentration of the inorganic acid solution used in the first reaction step ranges from 20 to 70 wt%, and a particularly preferred range is from 30 to 60 wt%. As the concentration of this acid is relatively low, the concentration can be readily attained by dehydration with less efforts than are required for concentrating a diluted acid solution to a highly concentrated acid. Needless to say, the aqueous solution of inorganic acid that is obtained in the first separation step may be immediately returned to the first reaction step if the concentration of the inorganic acid is within the range described above.

In the subsequent second reaction step (C), the reaction is preferably carried out in the presence of minimum water because water has bad influence on the reactivity of the reactants and the reaction rate. Water is particularly undesired if a carboxylic acid is used as the catalyst because this must be finally separated from water. Therefore, it is desired that as much water as possible should be removed from the organic-phase reaction mixture obtained in the first separation step. One method for attaining this object is by azeotropic distillation in the presence of an azeotropic agent. If an organic solvent is used in the first reaction step, distillation of water can be achieved simultaneously with the distillation of a portion of or all of this organic solvent.

In the second reaction step, the reaction is preferably performed in the substantial absence of a methylenating agent. If the organic-phase reaction mixture that has been subjected to phase separation and optional washing with water still contains a methylenating agent, the methylenating agent is preferably removed simultaneously with the removal of water from the mixture. However, if formaldehyde or its precursor which generates formaldehyde in the reaction system is used as a methylenating agent, it seldom occurs that such a methylenating agent is left in the organic-phase reaction mixture because formaldehyde or its precursor is in most cases water-soluble.

The organic-phase reaction mixture thus obtained is substantially free from the methylenating agent, but it does contain the intermediate compounds with the methylene-amino bond (—CH$_2$—N<), for example, bis(N-carboalkoxyanilino)methane and (N-carboalkoxyanilinomethyl)phenylcarbamate. The purpose of the second reaction step is to convert these compounds to diphenylmethane dicarbamates by an easy and simple method, and it is essential that in this second reaction step, the reaction must be carried out in the presence of N-phenylcarbamates. This object can be achieved by carrying out the intermolecular transfer reaction of the intermediate compounds with an N-phenylcarbamate, which reaction has been found for the first time by the present inventors.

As described before, one conventional method to convert these intermediate compounds having the methylene-amino bond to diphenylmethane dicarbamates and polymethylene polyphenylcarbamates has been proposed (see U.S. Pat. No. 4,146,727). This method, however, consists of the intramolecular rearrangement and condensation reactions of the intermediate compounds, so that it requiresd a very strong protonic acid having the equal strength of the 75% or more concentrated sulfuric acid or a very strong Lewis acid such as antimony pentafluoride, and it also requires a considerable length of the reaction time, in order to complete the reaction. On the other hand, according to the process of the present invention, the compounds having the methylene-amino bond are subjected to an intermolecular transfer reaction with an N-phenylcarbamate which may be the same as or different from the N-phenylcarbamate used as the starting material.

Therefore, the process of the present invention does not require the use of an acid as strong as what is used in the conventional method that depends on intramolecular rearrangement reaction of the compounds having the methylene-amino bond. Instead, the present invention uses a much weaker carboxylic acid having a pKa of not more than 4, preferably from 3 to −4, more preferably from 2.5 to −4, in an aqueous solution at 25° C. or solid acid. Even in the presence of this weak acid, the process of the present invention permits the intended reaction to proceed quantitatively at a fast rate, and the desired diphenylmethane dicarbamates can be obtained with high selectivity. This is one great feature of the present invention.

For the sake of clarity, the process of the intermolecular transfer reaction carried out in the second reaction step is illustrated below with reference to the case where an unsubstituted N-phenylcarbamate is reacted with the compound having the methylene-amino bond:

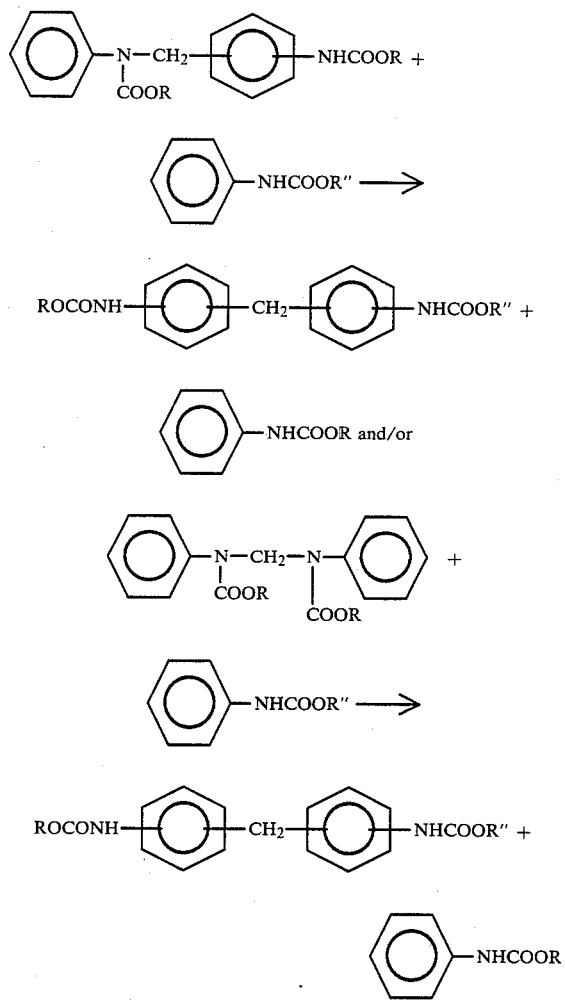

(wherein R″ may be the same or different from R).

As shown above, in the reaction between the dinuclear compound having the methylene-amino bond with the N-phenylcarbamate, the N-phenylcarbamate as one of the reactants is regenerated and a compound wherein R″ is replaced by R is also formed. But in any event, one of the reaction products obtained is a dinuclear diphenylmethane dicarbamate which can be used as a starting material for the production of diphenylmethane diisocyanates. In commercial operation, R and R″ are usually the same and the production of the above mentioned byproduct can be avoided.

The present inventors have also found that trinuclear and other polynuclear compounds having the methylene-amino bond can be converted to diphenylmethane dicarbamates as illustrated below.

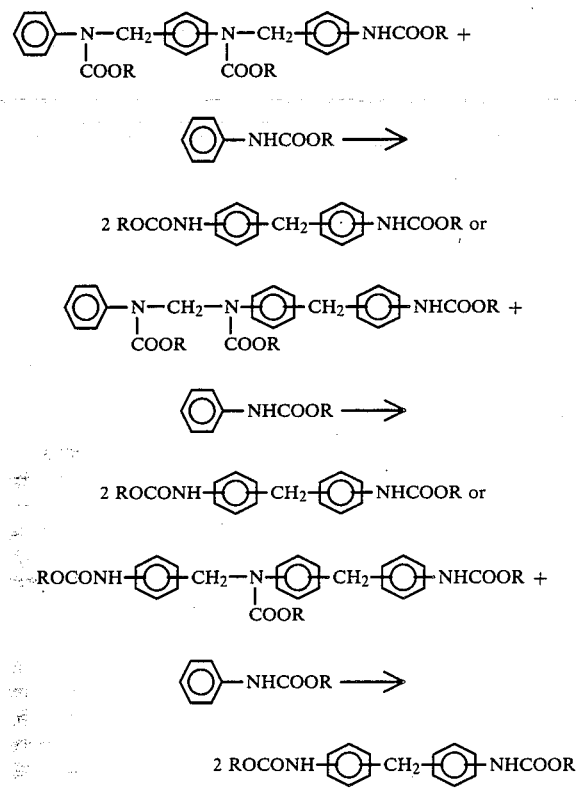

As will be understood from the reaction schemes for the reaction of the compounds having the methylene-amino bond, even if the compounds having the methylene-amino bond are reacted with an N-phenylcarbamate used in an amount less than one equivalent of the methylene-amino bond, the desired diphenylmethane carbamate can be produced, because an N-phenylcarbamate is also formed as a byproduct in the course of the intermolecular transfer reaction. However, in this case the reaction is slow. Therefore, in order to increase the reaction rate and enhance the selectivity for the diphenylmethane dicarbamates, the N-phenylcarbamate is preferably present during the intermolecular transfer reaction in an amount greater than one equivalent of the methylene-amino bond in the intermediate. If the amount of the N-phenylcarbamate remaining unreacted in the organic-phase reaction mixture is not sufficient for this purpose, an additional amount of the N-phenylcarbamate may preferably be incorporated in the second reaction step. For the purpose, N-phenylcarbamate is preferably present in an amount of from 1 to 200 mol equivalents, more preferably from 5 to 100 mol equivalents, per equivalent of the methylene-amino bond.

As described above, the greatest feature of the second reaction step is to use at least one catalyst selected from the group consisting of a carboxylic acid which has a pKa of not more than 4 in an aqueous solution at 25° C.,
and a solid acid. Suitable carboxylic acids meeting this requirement include formic acid; halogenated acetic acids such as fluoroacetic acid, difluoroacetic acid, trifluoroacetic acid, chloroacetic acid, dichloroacetic acid, trichloroacetic acid, bromoacetic acid, dibromoacetic acid, tribromoacetic acid, iodoacetic acid, diiodoacetic acid and triiodoacetic acid; α-halogenated and α,α-dihalogenated aliphatic carboxylic acids such as α-fluoropropionic acid, α,α-difluoropropionic acid, α-chloropropionic acid, α,α-dichloropropionic acid, α-fluorobutyric acid and α-chlorobutyric acid; α-cyano aliphatic carboxylic acids such as cyanoacetic acid, α-cyanopropionic acid and α-cyanobutyric acid; acylacetic acids such as acetoacetic acid, dichloroacetyl acetic acid and fluoroacetyl acetic acid; alkoxy acetic acids and phenoxy acetic acids such as methoxy acetic acid, ethoxy acetic acid, chlorophenoxy acetic acid (its isomers) and cyanophenoxy acetic acid (its isomers); halogenated benzoic acids such as chlorobenzoic acid (its isomers), fluorobenzoic acid (its isomers), difluorobenzoic acid (its isomers), bromobenzoic acid (its isomers) and trichlorobenzoic acid (its isomers); hydroxy benzoic acids such as salicylic acid, dihydroxy benzoic acid (its isomers) and trihydroxy benzoic acid (its isomers); nitrated benzoic acids such as nitrobenzoic acid and dinitrobenzoic acid; glycolic acid; lactic acid; malic acids such as malic acid, dimethyl malic acid and dihydroxy malic acid; tartaric acids such as tartatic acid, dimethyl tartaric acid and dihydroxy tartaric acid; citric acid; malonic acids such as malonic acid and dimethyl malonic acid; oxalic acid; maleic acid; fumaric acid; mandelic acid; phthalic acids such as phthalic acid (its isomers) and halogenated phthalic acid (its isomers); furancarboxylic acids; thiophencarboxylic acids; thioacetic acid; cyclopropane-1,1-dicarbaoxylic acids; sulfoacetic acids such as sulfoacetic acid and difluorosulfoacetic acid; halogenated malonic acids such as difluoromalonic acid and dichloromalonic acid; and halogenated succinic acids such as 1,2-difluorosuccinic acid, perfluorosuccinic acid and perchlorosuccinic acid. Among these carboxylic acids, halogenated acetic acids, α-halogenated and α,α-dihalogenated aliphatic carboxylic acids are preferred, with halogenated carboxylic acids wherein the halogen is chlorine or fluorine being particularly preferred. Fluorinated carboxylic acids are more preferred, and trifluoroacetic acid is most preferred.

Examples of the solid acid that can be used in the second reaction step are listed below: acidic clay minerals and inorganic cation exchangers such as acid clay, bentonite, kaolin, zeolite and montmorillonite; these acidic clay minerals and inorganic cation exchangers that have been treated with inorganic acids such as hydrofluoric acid, hydrochloric acid, perchloric acid and sulfuric acid, or ammonium salts of these acidic clay minerals and inorganic cation exchangers which have been subjected to protonation treatment by calcination; the solidified acids that are prepared by supporting liquid acids such as sulfuric acid, phosphoric acid, organic carboxylic acids and organic sulfonic acids or the heteropoly-acids such as dodecamolybdophosphoric acid, dodecamolybdosilicic acid, dodecatungstophosphoric acid, dodecatungstosilicilic acid and tungstomolybdophosphoric acid on carriers such as alumina, silica, silica-alumina, silica-alumina-zirconia, zirconia, titania, boria, zeolite, silica-titania, barium sulfate, calcium carbonate, asbestos, bentonite, diatomaceous earth, activated carbon, graphite, activated clay and acidic clay minerals, followed by heat treatment; solid sulfuric acid products that are prepared by first gelling water-soluble sols (e.g., alumina sol, silica-alumina sol and silica sol) in the presence of sulfuric acid, adding a large amount of sulfuric acid to dissolve the gel, and then cooling the solution to solidify, or precipitating a crystal from the solution, or heating the solid obtained to a temperature between 100° and 600° C.; metal oxides and mixed metal oxides such as silica, alumina, zinc oxide, titania, antimony oxide, silica-alumina, silica-titania, titania-alumina, and silica-zirconia; acidic solid sulfates, nitrates and phosphates such as nickel sulfate, aluminum sulfate, iron sulfate, chromium nitrate, bismuth nitrate, zirconium phosphate, aluminum phosphate, and these sulfates, nitrates and phosphates that are supported on the carriers listed above; organic cation exchange resins having at least one acidic group such as fluoroalkyl sulfonic acid group, fluoroalkyl carboxyl group or alkyl phosphoric acid group; and inorganic oxides having either —R'''—SO$_3$H or —R'''—COOH or both bound thereto.

As for the inorganic oxides having —R'''—SO$_3$H or —R'''—COOH bound thereto, those having a divalent organic residual group or organometallic compound residue as R''' and having not more than 30, especially not more than 20, carbon atoms are preferred. Suitable examples of the organic residual group include aliphatic hydrocarbon groups, aromatic hydrocarbon groups, aralkyl hydrocarbon groups, and fluoroalkyl groups, as well as those which have and ether bond, thioether bond, sulfone bond, carbonyl bond, ester bond, amido bond, imido bond or heterocyclic portion at terminal or in the backbone of these hydrocarbon groups. Suitable examples of the organometallic compound residues included those which have a metallic element bound to the terminal or backbone of the organic residual groups listed above. Organosilicon compound residues having a silicon atom at terminal, for example, those having a halosilyl or alkoxysilyl group bound to the terminal are advantageous because they are easy to prepare and form a stable bond with inorganic oxides.

The organic residual groups or organometallic compound residues listed above may have part of the hydrogen atoms present replaced by a halogen atom such as florine, chlorine or bromine, or substituents such as alkyl, alkoxy, aryl, aryloxy, hydroxyl, nitrile, alkoxycarbonyl, carboxyl and sulfonic acid groups. Advantageous inorganic oxides include those having a hydroxyl group on the surface such as silica, silica-alumina, alumina, titania, zirconia, magnesia, zeolite, diatomaceous earth, clay materials, glass, titania-alumina, silica-titania and silica-zirconia. Silica, porous glass and silica-alumina are particularly preferred.

Preferred examples of the solid acids include acidic clay minerals and inorganic cation exchangers, or these acidic solid materials that have been subjected to acid or protonation treatment; acidic metal oxides and mixed metal oxides, or these acidic solid materials that have been subjected to acid or protonation treatment; organic cation exchange resins having either a fluoroalkyl sulfonic acid groups or fluoroalkyl carboxyl groups or both; and inorganic oxides having an organic group bound thereto having either a sulfonic acid group or a carboxyl group or both. Particularly preferred solid acids are cation exchange resins having fluoroalkyl sulfonic acid resins and zeolite. It is not preferred to use the well-known sulfonated polyaromatic ion exchange resins having the framework made by copolymerization of styrene and divinylbenzene in the second reaction step, because the deterioration of the activities of those resins occurs in a short length of the reaction time. The reasons seem to be that the condensation products such as diphenylmethane dicarbamates and polymethylene polyphenylcarbamates are easiliy adsorbed on he resins and cover the acidic points of the resins, since those resins have a lot of benzene rings which have a strong affinity for polar aromatic compounds such as these condensation products. On the other hand, this problem is hard to occur in the case of the cation exchange resins having fluoroalkyl chains which are used in the present invention.

In the process of the present invention, these carboxylic acids and solid acids may be used either alone or in combination. There is no particular limitation on the amount in which these carboxylic acids and solid acids are used. If the reaction is carried out batchwise or if carboxylic acids are used in the flow process, the acids are preferably used in an amount of $10^{-3}$ to $10^4$ equivalents, more preferably $10^{-2}$ to $10^2$ equivalents, per equivalent of the methylene-amino group in the compounds having the methylene-amino bond. If the reaction is carried out in a flow reactor retaining a solid acid, the flow rate of the compound having the methylene-amino group preferably ranges from $10^{-3}$ to $10^4$ equivalents, more preferably from $10^{-2}$ to $10^3$ equivalents, per hour per liter of the solid acid. The carboxylic acid may be used in an excess amount so that it may also serve as a solvent.

The reaction temperature for the second reaction step generally ranges from 40° to 200° C., preferably from 60° to 180° C., and more preferably from 70° to 160° C. The reaction pressure generally ranges from 0.1 to 20 kg/cm$^2$, preferably from 0.5 to 10 kg/cm$^2$ and more preferably from 0.8 to 5 kg/cm$^2$. The reaction period varies with the type and amount of the acid catalyst used, the reaction temperature, the amount of the compound present having the methylene-amino bond, the amount of the N-phenylcarbamate present, and the nature of the specific reaction process (whether batchwise, continuous or flow process). Usually, the reaction continues for a period of several minutes to several hours, but in almost all cases, the reaction in the second reaction step can be completed within one hour. The reaction may be performed batchwise or in a continuous manner. If the acid catalyst consists of only a carboxylic acid, the reaction liquor may simply be passed through a flow reactor held at a predetermined temperature. If the acid catalyst consists of a solid acid, either the batchwise or flow process may be employed, and in either case, the solid acid is preferably retained within the reactor, or the solid acid is separated by a solid-liquid separator that immediately follows the reactor and is then returned to the reactor. The solid acid may be retained within the reactor by either fluidizing the acid within the reaction liquor or by fixing a catalyst bed of the acid in the reactor. Whichever reaction process is used, the solid acid permits a very easy separation from the reaction solution. Therefore, if the solid acid is used, the second reaction step can be combined with the second separation step into practically a single step, and the desired diphenylmethane dicarbamate can be directly obtained from the second reaction step.

The reaction in the second reaction step may be performed without solvents, but if desired, it may be carried out in the presence of a suitable solvent. Illustrative solvents include aliphatic or alicyclic hydrocarbons such as pentane, hexane, heptane, octane, nonane, decane, n-hexadecane, cyclopentane and cyclohexane; halogenated hydrocarbons such as chloroform, ethylene chloride, carbon tetrachloride, dichloroethane, trichloroethane and tetrachloroethane; alcohols such as methanol, ethanol, propanol and butanol; aromatic compounds such as benzene, toluene, xylene, ethylbenzene, monochlorobenzene, dichlorobenzene, bromonaphthalene, nitrobenzene, and o-, m- or p-nitrotoluene; ethers such as diethyl ether, 1,4-dioxane and tetrahydrofuran; esters such as methyl acetate, ethyl acetate and methyl formate; and sulfolanes such as sulfolane, 3-methylsulfolane and 2,4-dimethylsulfolane. Also usable are aliphatic carboxylic acids such as acetic acid and propionic acid, and halogenated aliphatic carboxylic acids such as monochloroacetic acid, dichloroacetic acid, trichloroacetic acid and trifluoroacetic acid. Acid anhydrides of these carboxylic acids may also be used. If an organic solvent is used in the first reaction step, it may also be used in the second reaction step.

If a carboxylic acid is used in the second reaction step, it is separated from the reaction mixture in the subsequent second separation step, and a condensation product containing the desired diphenylmethane dicarbamate and sometimes a small amount of its higher homolog (i.e., polymethylene polyphenylcarbamate) is obtained. This ease of separation of the carboxylic acid is another great feature of the present invention. As already mentioned, α-halogenated carboxylic acids are preferred carboxylic acids, and of the α-halogenated carboxylic acids, trichloroacetic acid and trifluoroacetic acid are particularly preferred. These acids have boiling points lower than the N-phenylcarbamate used as the starting material and the diphenylmethane dicarbamate formed as the reaction product, and therefore they can be easily separated from the reaction mixture. The carboxylic acid thus separated in the second separation step is returned for further use in the second reaction step either immediately or after being properly adjusted for its composition.

Therefore, it is also a great feature of the present invention that the acid catalyst used in the second reaction step, whether it is a solid acid or carboxylic acid, can be separated very easily from the reaction solution.

If the solvents other than the carboxylic acids listed above are used in the second reaction step, they may optionally be separated by distillation, preferably under 200° C., so as to obtain the desired product. If necessary, any N-phenylcarbamates that remain unreacted in the reaction mixture can also be separated from the latter by a suitable method such as distillation, preferably under 200° C.

The so-obtained condensation product of N-phenylcarbamates mainly consists of the dinuclear diphenylmethane dicarbamate and contains little or no trinuclear dimethylene triphenylcarbamates. The selectivity for the desired diphenylmethane dicarbamate is over 80%.

The present invention ensures an industrially advantageous methods for the production of diphenylmethane dicarbamates with extremely high selectivity from N-phenylcarbamates. These compounds are highly suitable for use as starting materials for the production of diphenylmethane dissocyanates by thermal decomposition.

The present invention is hereunder described in greater detail by reference to working examples, to which the scope of the present invention is by no means limited. In the examples, the reaction products obtained were analyzed by high-performance liquid chromatography.

EXAMPLE 1

A 100-ml glass flask was charged with 50 wt% sulfuric acid (60 g), ethyl N-phenylcarbamate (19 g) and 37% aqueous formaldehyde (1.9 g). The mixture was heated at 90° C. for 2 hours with vigorous stirring. Thereafter, the reaction mixture was transferred into a separating funnel to be separated into an organic layer and an aqueous layer. The organic layer was washed with warm water and then the small amount of water contained was removed by a rotary evaporator. The washings were combined with the previously separated aqueous layer, and then the predetermined amount of water was removed from the mixture by a rotary evaporator so as to recover 50 wt% sulfuric acid (60 g).

Analysis of the organic layer showed that the conversion of the ethyl N-phenylcarbamate was 38.5%, and the reaction product comprised 30.1 wt% of diethyl 4,4'-diphenylmethane dicarbamate, 4 wt% of diethyl 2,4'-diphenylmethane dicarbamate, 1.9 wt% and 2.4 wt% of bis-(N-carboethoxyanilino)methane and ethyl(N-carboethoxyanilinomethyl)phenylcarbamate each having a methylene-amino bond, and 0.9 wt% of trinuclear and other polynuclear compounds. No formaldehyde was detected in the organic layer. To the organic layer was added trifluoroacetic acid (15 g), and the mixture was stirred at 75° C. for 20 minutes. Thereafter, the trifluoroacetic acid was separated by distillation. The resulting reaction mixture consisted of ethyl N-phenylcarbamate (60.2 wt%), diethyl 4,4'-diphenylmethane dicarbamate (34.5 wt%), diethyl 2,4'-diphenylmethane dicarbamate (4.2 wt%), and trinuclear triethyl dimethylenetriphenylcarbamate (1.1 wt%). No compound having a methylene-amino bond was detected. The condensation product had the following selectivities: 87.5% for diethyl 4,4'-diphenylmethane dicarbamate, 10.7% for diethyl 2,4'-diphenylmethane dicarbamate, and 1.8% for triethyl dimethylenetriphenylcarbamate. The total selectivity for the dinuclear diethyl diphenylmethane dicarbamates was therefore 98.2%. In Example 1, 14.95 g of trifluoroacetic acid was separated by distillation and could be immediately put to another use.

EXAMPLE 2

A 400-ml glass reactor was charged with 45 wt% sulfuric acid (200 g), methyl N-phenylcarbamate (50 g), 37% aqueous formaldehyde (5.5 g) and nitrobenzene (50 g: solvent). The mixture was heated at 90° C. for 2 hours with vigorous stirring. Thereafter, the reaction mixture was separated into an organic layer and an aqueous layer. The organic layer was washed with warm water to remove the small amount of residual sulfuric acid, and subsequently, the small amount of water was removed by azeotropic distillation with part of nitrobenzene. Analysis of the organic layer showed that the conversion of the methyl N-phenylcarbamate was 41%, and the yields of the condensation products were as follows: 32% of dimethyl 4,4'-diphenylmethane dicarbamate, 2.8% of dimethyl 2,4'-diphenylmethane dicarbamate, and 2.9% and 3.3% of bis(N-carbomethoxyanilino)methane and methyl(N-carbomethoxy anilinomethyl)phenyl carbamate each having a methylene-amino bond. No trinuclear and other polynuclear compounds were present. The aqueous layer was concentrated as in Example 1 and put to another use. No formaldehyde was detected in the organic layer.

Trifluoroacetic acid (40 g) was added to the organic layer and the resulting solution was passed through the bottom of a reactor (ID: 10 mm; height: 30 cm; temp.: 80° C.) at a rate of 1 ml/min. The reaction liquor was freed of trifluoroacetic acid and nitrobenzene by distillation under reduced pressure at a temperature lower than 150° C. The resulting reaction mixture contained 58 wt% of methyl N-phenylcarbamate, 37.6 wt% of dimethyl 4,4'-diphenylmethane dicarbamate and 4.4 wt% of dimethyl 2,4'-diphenylmethane dicarbamate. However, no trinuclear compound, i.e., trimethyl dimethylenetriphenylcarbamate was present.

EXAMPLE 3

A mixture of ethyl N-phenylcarbamate (16 wt%), formaldehyde (0.6 wt%), sulfuric acid (33 wt%), nitrobenzene (17 wt%) and water (33.4 wt%) was fed through a continuous reactor (for its construction, see FIG. 1) in order to carry out condensation of the ethyl N-phenylcarbamate. The reaction was performed at 90° C. in the first reaction step, and at 80° C. in the second reaction step. In the second reaction step, trifluoroacetic acid was added so that its content in the liquid reaction mixture was 28 wt%. The residence time was 3 hours for the first reaction step and 15 minutes for the second reaction step. The resulting condensation product had the following selectivities: 88% for diethyl 4,4'-diphenylmethane dicarbamate, 10% for diethyl 2,4'-diphenylmethane dicarbamate, and 2% for the trinuclear compound (i.e., triethyl dimethylenetriphenylcarbamate).

EXAMPLE 4

Ethyl N-phenylcarbamate was condensed through the first reaction and separation steps as in Example 1. The resulting reaction mixture had the same composition as the Example 1. The mixture was incorporated with nitrobenzene (30 g) and beads of fluorinated sulfonic acid resin (2 g) having the following repeating unit:

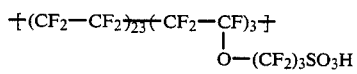

The mixture was then stirred for 10 minutes at 110° C. The fluorinated sulfonic acid resin was separated from the reaction mixture by filtration. The reaction mixture no longer contained a compound having the methyleneamino bond. The condensation product had the following selectivities: 88.5% for diethyl 4,4'-diphenylmethane dicarbamate, 10.4% for diethyl 2,4'-diphenylmethane dicarbamate and 1.1% for the trinuclear compound (i.e., triethyl dimethylenetriphenyl carbamate). Therefore, the total selectivity for the dinuclear compounds (i.e., diethyl diphenylmethane dicarbamates) was 98.9%.

The fluorinated sulfonic acid resin separated by filtration could be immediately put to another cycle of the second reaction, with the results being almost the same as in the first cycle.

EXAMPLE 5

Methyl N-phenylcarbamate was condensed through the first reaction and separation steps as in Example 2. The resulting reaction had the same composition as in Example 2. The mixture was continuously fed through the bottom of a reactor (120° C.) at a rate of 0.5 ml/min. The reactor was made of a stainless steel tube (ID: 10 mm; height: 30 cm) and filled with SK-500 (Y type zeolite produced by Union Carbide Corporation that was partially ion-exchanged by rare earth elements). The reaction liquor drawn from the top of the reactor did not contain any compound having the methyleneamino bond. It was then freed of nitrobenzene by distillation under reduced pressure at a temperature lower than 150° C. The resulting reaction mixture contained 57 wt% of methyl N-phenylcarbamate, 38 wt% of dimethyl 4,4'-diphenylmethane dicarbamate and 5 wt% of dimethyl 2,4'-diphenylmethane dicarbamate. No trinuclear compound (i.e., trimethyl dimethylenetriphenyl carbamate) was present.

EXAMPLE 6

Figure 2:
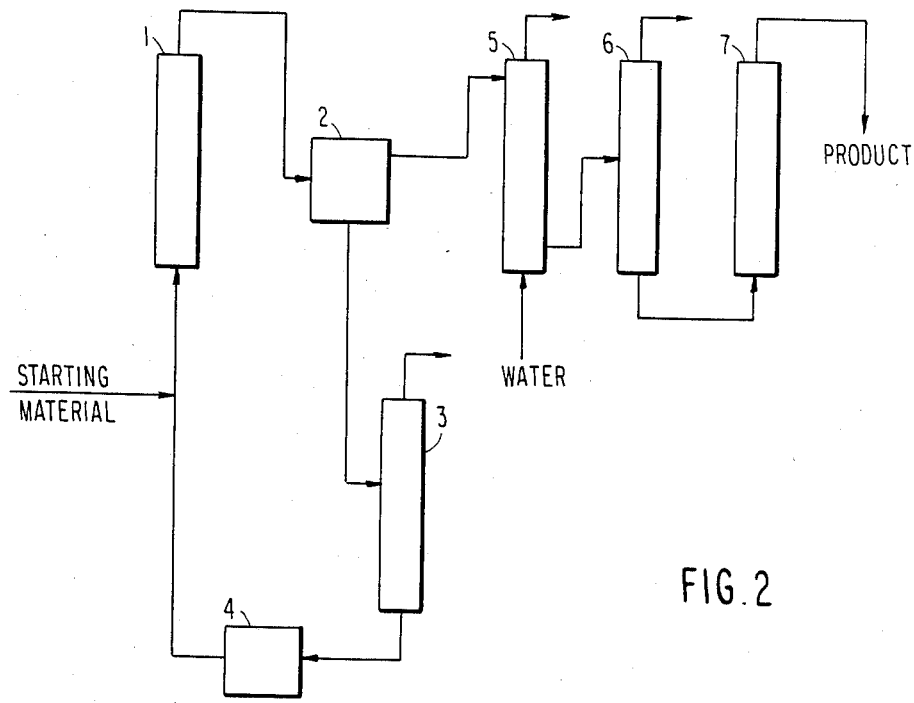
FIG. 2 is a schematic flow diagram of another preferred embodiment of the process of the present invnetion.

A feed mixture having the same composition as used in Example 3 was subjected to condensation in a continuous reactor of the type shown in FIG. 2. The reaction temperature was 90° C. for the first reaction step and 120° C. for the second reaction step. In the second reaction step, a reaction tube filled with a carboxyl-containing fluorinated sulfonic acid resin having the following repeating unit was used:

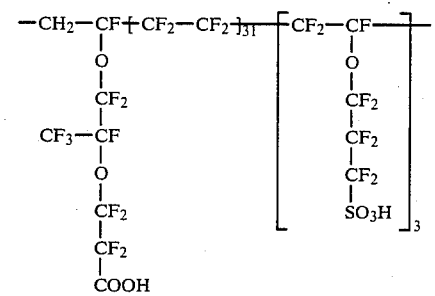

This resin was prepared by forming a terpolymer from tetrafluoroethylene, a compound having the formula:

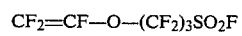

and a compound having the formula:

then reacting the terpolymer with a mixture of methanol, sodium hydroxide and water, and finally ion-exchanging the reaction product with hydrochloric acid.

The residence time was 2 hours for the first reaction step and 15 minutes for the second reaction step. The finally obtained condensation product had the following selectivities: 89% for diethyl 4,4'-diphenylmethane dicarbamate, 9% for diethyl 2,4'-diphenylmethane dicarbamate, and 2% for the trinuclear compound (i.e., triethyl dimethylenetriphenylcarbamate).

EXAMPLE 7

A 400-ml glass flask was charged with 50 wt% sulfuric acid (77 g), ethyl N-phenylcarbamate (64.8 g), 37% aqueous formaldehyde (10.6 g) and nitrobenzene (130 g). The reactants were heated at 90° C. for 2 hours with vigorous stirring. Therefore, the reaction mixture was separated into an organic layer and an aqueous layer. The organic layer was washed with warm water to remove the small amount of residual sulfuric acid. Then, the small amount of water was removed from the organic layer by azeotropic distillation with a portion of the nitrobenzene. Analysis of the organic layer showed that the conversion of the ethyl N-phenylcarbamate was 41%, and the reaction product had the following selectivities: 70.1% for diethyl 4,4'-diphenylmethane dicarbamate, 7.2% for diethyl 2,4'-diphenylmethane dicarbamate, 16% for ethyl (N-carboethoxyanilinomethyl)phenyl carbamate having the methylene-amino bond, and 6.7% for trinuclear compounds including the one having the methylene-amino bond. The aqueous layer was concentrated as in Example 1 and put to another use. No formaldehyde was detected in the organic layer.

Trifluoroacetic acid (65 g) was added to the organic layer and the mixture was passed through the second reaction and separation steps as in Example 2. The percent conversion of the ethyl N-phenylcarbamate increased to 47%, and the selectivities for diethyl 4,4'- and 2,4'-diphenylmethane dicarbamates to 87.2% and 8.6%, respectively, whereas the selectivity for the trinuclear compounds dropped to 4.2%. Neither dinuclear nor trinuclear compound having the methylene-amino bond was present.

EXAMPLE 8

Ethyl N-phenylcarbamate was passed through the first reaction and separation steps as in Example 7 except that nitrobenzene was replaced by 130 g of o-dichlorobenzene and the amount of 37% aqueous formaldehyde was increased to 15.9 g. The conversion of the ethyl N-phenylcarbamate was 47.6%, and the reaction product had the following selectivities: 65.2% and 6.2% for diethyl 4,4'- and 2,4'-diphenylmethane dicarbamates, respectively, 18.1% for ethyl (N-carboethoxyanilinomethyl)phenyl carbamate and 10.5% for trinuclear compounds containing the one having the methylene-amino bond.

Trifluoroacetic acid (50 g) was added to the reaction product and the mixture was passed through the second reaction and separation steps as in Example 2. The conversion of ethyl N-phenylcarbamate increased to 62.6%, and the selectivities for diethyl 4,4'- and 2,4'-diphenylmethane dicarbamates to 83.2% and 8.3%, respectively, whereas the selectivity for the trinuclear compounds dropped to 8.5%. Neither dinuclear nor trinuclear compounds having the methylene-amino bond were present.

EXAMPLE 9

Ethyl N-phenylcarbamate was passed through the first reaction and separation steps as well as the second reaction and separation steps as in Example 7 except that nitrobenzene was replaced by 130 g of chlorobenzene and the amount of 37% aqueous formaldehyde was reduced to 8 g. The conversion of the ethyl N-phenylcarbamate was 42%, and the final reaction product had the following selectivities: 88.2% and 8.7% for diethyl 4,4'- and 2,4'-diphenylmethane dicarbamates and 3.1% for the trinuclear compounds.

EXAMPLE 10

A feed mixture consisting of ethyl N-phenylcarbamate (23 wt%), formaldehyde (1.4 wt%), sulfuric acid (13.6 wt%), nitrobenzene (46 wt%) and water (16 wt%) was subjected to condensation reaction in a continuous reactor of the type shown in FIG. 1. The reaction was carried out at 90° C. in the first reaction step, and at 80° C. in the second reaction step. In the second reaction step, trifluoroacetic acid was added so that its content in the reaction liquor was 25 wt%. The residence time was 2 hours for the first reaction step and 15 minutes for the second reaction step. The conversion of the ethyl N-phenylcarbamate was 45%. The resulting condensation product had the following selectivities: 87% for diethyl 4,4'-diphenylmethane dicarbamate, 8% for diethyl 2,4'-diphenylmethane dicarbamate and 5% for a trinuclear compound (i.e., triethyl dimethylenetriphenylcarbamate).

EXAMPLE 11

Ethyl N-phenylcarbamate was passed through the first reaction and separation steps as in Example 1. To the organic layer of the resulting reaction mixture, trichloroacetic acid (21 g) was added and stirred at 80° C. for 1 hour. The condensation product obtained by distilling off the trichloroacetic acid under reduced pressure at a temperature lower than 150° C. had the following selectivities: 86.8% for diethyl 4,4'-diphenylmethane dicarbamate, 11.5% for diethyl 2,4'-diphenylmethane dicarbamate, and 1.7% for trinuclear compounds.

EXAMPLE 12

Ethyl N-phenylcarbamate was passed through the first reaction and separation steps as in Example 1. To the organic layer of the resulting reaction mixture, nitrobenzene (40 g) and aluminum sulfate powder (5 g) were added and stirred for 40 minutes at 150° C. After removing the aluminum sulfate from the reaction mixture by filtration, the nitrobenzene was distilled off under reduced pressure at a temperature lower than 150° C. The final condensation product had the following selectivities: 81.5% for diethyl 4,4'-diphenylmethane dicarbamate, 13.3% for diethyl 2,4'-diphenylmethane dicarbamate and 5.2% for trinuclear compounds.

EXAMPLE 13

Silica gel (100 g) was suspended in toluene (300 ml), and 3-chloropropyltrimethoxy silane (80 ml) was added to the suspension. The resulting mixture was stirred for 5 hours at the refluxing temperature in a nitrogen atmosphere. The reaction product was filtered, subjected to Soxhlet extraction with methanol for 15 hours, and vacuum-dried. The resulting chloropropyl silica was mixed with a saturated aqueous solution of sodium sulfite (1,000 ml) and the mixture was stirred for 24 hours under reflux in a nitrogen atmosphere. After cooling, the silica product was separated out and washed with distilled water to remove the residual sulfite salt. The silica product was then treated with 1N nitric acid, washed with distilled water and vacuum-dried. The silica product hereinafter referred to as sulfopropyl silica contained 0.9 wt% of sulfur.

A feed liquor having the same composition as used in Example 10 was subjected to condensation in a reactor of the type shown in FIG. 2 that included a vessel for the second reaction step filled with the sulfopropyl silica. The reaction temperature was 90° C. for the first reaction step and 120° C. for the second reaction step. The residence time was 2.5 hours for the first reaction and 20 minutes for the second reaction. The final condensation product had selectivities which were substantially the same as those achieved in Example 10.

EXAMPLE 14

Zirconium oxychloride ($ZrOCl_2$) was hydrolyzed with 28% ammonia water, and the resulting precipitate was thoroughly washed with deionized water and dried at 100° C. for 24 hours to provide $Zr(OH)_4$. The hydroxide was ground into particles. After placing the particles on a sheet of filter paper, 1N sulfuric acid (30 ml) was poured over the particles and left to stand for a certain period. After drying with air, the particles were collected from the filter paper and calcined at 650° C. for 3 hours in air, thereby producing a solid acid ($SO_4^{2-}/ZrO_2$) having sulfate ions.

Ethyl N-phenylcarbamate was subjected to condensation as in Example 12 except that the above prepared solid acid was used as a catalyst in the second reaction step. The final condensation product had selectivities which were substantially the same as those attained in Example 12.

EXAMPLE 15

This example shows that the intermolecular transfer reaction occurs in the second reaction step. Ethyl N-phenylcarbamate was passed through the first reaction and separation steps as in Example 1. The intermediate compounds consisting of bis-(N-carboethoxyanilino)methane (2 g) and ethyl (N-carboethoxyanilinomethyl)phenylcarbamate (2.5 g) were separated by a column chromatography. A 100-ml glass flask was charged with these intermediate compounds (4.5 g), trifluoroacetic acid (5 g), methyl N-phenylcarbamate (5 g), and nitrobenzene (30 ml). The mixture was stirred at 75° C. for 15 minutes. Thereafter, the trifluoroacetic acid and the nitrobenzene were removed by distillation under reduced pressure at a temperature lower than 150° C. The resulting reaction mixture consisted of diphenylmethane dicarbamate having both ethyl and methyl groups (3.15 g, slectivity of 73%), diethyl diphenylmethane dicarbamate (0.86 g, selectivity of 19%), dimethyl diphenylmethane dicarbamate (0.33 g, selectivity of 8%), methyl N-phenylcarbamate (3.23 g), and ethyl N-phenylcarbamate (1.93 g). The intermediate compounds and polynuclear compounds other than dinuclear compounds were not detected.

It is clearly seen that the reaction proceeded intermolecularly by the following facts, that is, the cross-coupled diphenylmethane dicarbamate with both ethyl and methyl group is a main product and ethyl N-phenylcarbamate is freed from the intermediate compounds in a yield of 44.5% based on the ethyl N-phenylcarbamate moiety in the original intermediate compounds, and the reaction is very fast compared with the intramolecular rearrangement reaction.

While the invention has been described in detail and with reference to specific embodiment thereof, it will be apparent to one skilled in the art that various changes and modifications can be made therein without departing from the spirit and scope thereof.

What is claimed is:

1. A process for producing a diphenylmethane dicarbamate, comprising the steps of:

a first reaction Step (A) for reacting a methylenating agent in liquid phase with at least 2 mols of an N-phenylcarbamate per mol equivalent of the methylene group of the methylenating agent in the presence of an aqueous solution containing 20 to 70 wt% of an inorganic acid selected from the group consisting of hydrochloric acid, sulfuric acid, phosphoric acid, polyphosphoric acid, hetero poly-acid, and boric acid, at a temperature of 40° to 150° C., to obtain a first reaction mixture;

a first separation Step (B) for separating the first reaction mixture into the aqueous solution of an inorganic acid and an organic-phase reaction mixture substantially free from the inorganic acid;

a second reaction Step (C) for reacting the organic-phase reaction mixture under heat treatment at a temperature of 40° to 200° C. with an N-phenylcarbamate and in the presence of a carboxylic acid having a pKa of not more than 4 or a solid acid or a mixture of said carboxylic acid and said solid acid;

wherein the carboxylic acid is selected from the group consisting of formic acid, halogenated acetic acids, α-halogenated or α,α-dihalogenated aliphatic carboxylic acids, α-cyanoaliphatic carboxylic acids, acylacetic acids, alkoxy- or phenoxyacetic acids, halogenated benzoic acids, hydroxybenzoic acids, nitrated benzoic acids, glycolic acid, lactic acid, malic acids, tartaric acids, citric acid, malonic acid, maleic acid, fumaric acid, mandelic acid, phthalic acid, halogenated phthalic acids, furancarboxylic acids, thiophencarboxylic acids, thioacetic acid, cyclopropane-1,1-dicarboxylic acids, sulfoacetic acids, halogenated malonic acids, and halogenated succinic acids, and wherein the solid acid is selected from the group consisting of (i) acidic clay minerals and inorganic cation exchangers, or these acidic clay minerals and inorganic cation exchangers that have been treated with inorganic acids, and ammonium salts of these acidic clay minerals and inorganic cation exchangers which have been subjected to protonation treatment by calcination;

(ii) solidified acids that are prepared by supporting liquid acids on a carrier, followed by heat treatment;

(iii) solid sulfuric acid products that are prepared by first gelling water-soluble sols in the presence of sulfuric acid, adding sulfuric acid to dissolve the gel, and then cooling the solution to solidify, or precipitating a crystal from the solution, or heating the solid obtained to a temperature between 100° and 600° C.;

(iv) metal oxides or mixed metal oxides;

(v) acidic solid sulfates, nitrates, and phosphates, or these sulfates, nitrates and phosphates that are supported on a carrier;

(vi) organic cation exchange resins having at least one acidic group of fluoroalkyl sulfonic acid group, fluoroalkyl carboxylic acid group or alkyl phosphoric acid group; and (vii) inorganic oxides having either $—R'''—SO^3—H$ or $—R'''—COOH$ or both bound thereto wherein $R'''$ is a divalent organic residual group or organometallic compound having not more than 30 carbon atoms;

in order to convert intermediate compounds having a methylene amino bond to the desired diphenylmethane dicarbamates by the intermolecular transfer reaction of the intermediate compounds with the N-phenylcarbamate, whereby a second reaction mixture is obtained; and a second separation Step (D) for separating the acid away from the second reaction mixture to obtain a diphenylmethane dicarbamate, said N-phenylcarbamate used in Step (A) to (C), which may be the same or different, being represented by the formula (I):

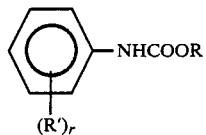

wherein R is an alkyl group having from 1 to 20 carbon atoms, an aromatic group or an alicyclic group having 3 to 30 carbon atoms; R' is hydrogen or a substituent selected from the group consisting of an alkyl group having from 1 to 20 carbon atoms, halogen atom, nitro group, cyano group, an alkoxy group having from 1 to 20 carbon atoms and an alicyclic group havng from 3 to 20 carbon atoms, provided that said substituents are bonded at the ortho- or meta-position to the urethane group; r is an integer of 0 to 4; when r is 2 or more, R' may represent the same or different substituents; and at least one hydrogen in R may be substituted by any of said substituents.

2. A process as claimed in claim 1, wherein the first reaction step (A) is carried out in the presence of an aqueous solution of inorganic acid in combination with an organic solvent.

3. A process as claimed in claim 1, wherein the inorganic acid is sulfuric acid.

4. A process as claimed in claim 1, wherein the first reaction step (A) is carried out by reacting a methylenating agent with 2 to 10 mols of an N-phenylcarbamate per mol equivalent of the methylene group of the methylenating agent.

5. A process as claimed in claim 1, wherein the methylenating agent is selected from the group consisting of formaldehyde, paraformaldehyde, trioxane and dialkoxymethane.

6. A process as claimed in claim 5, wherein the methylenating agent is an aqueous solution of formaldehyde.

7. A process as claimed in claim 2, wherein the organic solvent used in the first reaction step (A) has a boiling point of not higher than 300° C. at atmospheric pressure and has a mutual solubility with water of not more than 10% at room temperature.

8. A process as claimed in claim 7, wherein the organic solvent is an aromatic compound having a halogen atom.

9. A process as claimed in claim 7, wherein the organic solvent is an aromatic compound having at least one electron attracting substituent.

10. A process as claimed in claim 9, wherein the electron attracting substituent is a nitro group.

11. A process as claimed in claim 7, wherein the organic solvent is a compound selected from the group consisting of nitrobenzene, chlorobenzene and dichlorobenzene.

12. A process as claimed in claim 1, wherein the carboxylic acid used in the second reaction step (C) is α-halogenated carboxylic acid.

13. A process as claimed in claim 12, wherein the halogen in the α-halogenated carboxylic acid is selected from the group consisting of chlorine and fluorine.

14. A process as claimed in claim 13, wherein the α-halogenated carboxylic acid is trifluoroacetic acid.

15. A process as claimed in claim 1, wherein the solid acid is a cation exchange resin having fluoroalkyl sulfonic acid groups.

16. A process as claimed in claim 1, wherein the first separation step (B) is carried out until the organic-phase reaction mixture is substantially free of the methylenating agent, and the separated aqueous solution of the inorganic acid is returned to the first step (A) after optionally adjusting the concentration of the inorganic acid to a predetermined value.

17. A process as claimed in claim 16, wherein the acid in the second reaction step (C) is a carboxylic acid having a pKa of not more than 4 in an aqueous solution at 25° C.

18. A process as claimed in claim 1, wherein the methylenating agent is selected from the group consisting of formaldehyde, paraformaldehyde, trioxane, tetraoxane, dialkoxymethane, diacyloxymethane, 1,3-dioxolane, 1,3-dioxane, 1,3-dithiane, 1,3-oxathiane, and hexamethylenetetramine.

19. A process as claimed in claim 1, wherein the inorganic acid is present in an amount of 0.01 to 20 mol equivalents per mol equivalent of the N-phenylcarbamate in step (A).

20. A process as claimed in claim 1, wherein the reaction pressure in step (A) is 0.5 to 20 kg/cm$^2$.

21. A process as claimed in claim 1, wherein the N-phenylcarbamate is present in an amount of 1 to 200 mol equivalents per equivalent of the methylene-amino bond in the intermediate compounds in step (C).

22. A process as claimed in claim 1, wherein the acid is present in an amount of $10^{-3}$ to $10^4$ equivalent per equivalent of the methylene-amino group in the intermediate compound in step (C).

23. A process as claimed in claim 1, wherein the reaction pressure in step (C) is 0.1 to 20 kg/cm$^2$.

24. A process as claimed in claim 1, wherein the solid acid is an inorganic cation exchanger.

25. A process as claimed in claim 24, wherein the solid acid is zeolite.

26. A process as claimed in claim 25, wherein the second separation step (D) involves separating away the carboxylic acid which is then returned to the second reaction step (C).

27. A process for producing a diphenylmethane dicarbamate comprising the steps of:

a first reaction Step (A) for reacting a methylenating agent in a liquid phase with 2 to 10 mols of an N-phenylcarbamate per mol of equivalent of the methylene group of the methylenating agent in the presence of an aqueous solution containing 20 to 70 wt% of an inorganic acid selected from the group consisting of hydrochloric acid, sulfuric acid, phosphoric acid, polyphosphoric acid, hetero poly-acid and boric acid, with or without an organic solvent at a temperature of 40° to 150° C., to obtain a first reaction mixture;

a first separation Step (B) for separating the first reaction mixture into the aqueous solution of an inorganic acid and an organic-phase reaction mixture substantially free from the inorganic acid and the methylenating agent, the separated aqueous solution of the inorganic acid being returned to the first reaction Step (A) after optionally adjusting the concentration of the inorganic acid to a predetermined value; and a second combination reaction/separation Step (E) wherein a reaction and a separation are simultaneously and continuously carried out by first bringing the organic-phase reaction mixture separated in the first separation Step (B) into contact with a solid acid that is retained within a reactor at a temperature between 40° and 200° C. in the presence of an N-phenylcarbamate to convert intermediate compounds having a methylene-amino bond to the desired diphenylmethane dicarbamates by the intermolecular transfer reaction of the intermediate compounds with the N-phenylcarbamate, and subsequently withdrawing the resulting reaction mixture from the reactor, wherein the solid acid is selected from the group consisting of (i) acidic clay minerals and organic cation exchangers, or these acidic clay minerals and inorganic cation exchangers that have been treated with inorganic acids, and ammonium salts of these acidic clay minerals and inorganic cation exchangers which have been subjected to protonation treatment by calcination;

(ii) solidified acids that are prepared by supporting liquid acids on a carrier, followed by heat treatment;

(iii) solid sulfuric acid products that are prepared by first gelling water-soluble sols in the presence of sulfuric acid, adding sulfuric acid to dissolve the gel, and then cooling the solution to solidify, or precipitating a crystal from the solution, or heating the solid obtained to a temperature between 100° and 600° C.;

(iv) metal oxides or mixed metal oxides;

(v) acidic solid sulfates, nitrates, and phosphates, or these sulfates, nitrates and phosphates that are supported on a carrier;

(vi) organic cation exchange resins having at least one acidic group of fluoroalkyl sulfonic acid group, fluoroalkyl carboxylic acid group or alkyl phosphoric acid group; and (vii) inorganic oxides having either $-R'''-SO^3-H$ or $-R'''-COOH$ or both bound thereto wherein $R'''$ is a divalent organic residual group or organometallic compound having not more than 30 carbon atoms, said N-phenylcarbamate used in Steps (A) and (E), which may be the same or different, being represented by the formula (I):

wherein R is an alkyl group having from 1 to 20 carbon atoms, an aromatic group or an alicyclic group having 3 to 30 carbon atoms; R' is hydrogen or a substituent selected from the group consisting of an alkyl group having from 1 to 20 carbon atoms, halogen atom, nitro group, cyano group, an alkoxy group having from 1 to 20 carbon atoms and an alicyclic group having from 3 to 20 carbon atoms, provided that said substituents are bonded at the ortho- or meta-position to the urethane group; r is an integer of 0 to 4; when r is 2 or more, R' may represent the same or different substituents; and at least one hydrogen in R may be substituted by any of said substituents.

28. A process as claimed in claim 27, wherein the aqueous solution of inorganic acid is a 40 wt% to 60 wt% aqueous solution of sulfuric acid.

29. A process as claimed in claim 27, wherein the methylanating agent is an aqueous solution of formaldehyde.

30. A process as claimed in claim 27, wherein the organic solvent is selected from the group consisting of nitrobenzene and dichlorobenzene.

31. A process as claimed in claim 27, wherein the solid acid is an inorganic cation exchanger.

32. A process as claimed in claim 31, wherein the solid acid is zeolite.

33. A process as claimed in claim 27, wherein the solid acid is a cation exchange resin having fluoroalkyl sulfonic acid groups.

* * * * *